(12) United States Patent
Li

(10) Patent No.: US 10,537,483 B2
(45) Date of Patent: Jan. 21, 2020

(54) LIQUID-ABSORBING BREATHABLE BLOOD-RESISTANT NO-LEAKAGE SANITARY PAD

(71) Applicant: Hangzhou Yuhong Sanitary products Co., Ltd., Hangzhou (CN)

(72) Inventor: Xinhua Li, Hangzhou (CN)

(73) Assignee: Hangzhou Yuhong Sanitary Products Co., Ltd., Hangzhou (CN)

( * ) Notice: Subject to any disclaimer, the term of this patent is extended or adjusted under 35 U.S.C. 154(b) by 325 days.

(21) Appl. No.: 15/275,508

(22) Filed: Sep. 26, 2016

(65) Prior Publication Data

US 2017/0319406 A1  Nov. 9, 2017

(30) Foreign Application Priority Data

May 3, 2016  (CN) .......................... 2016 1 0294096

(51) Int. Cl.
  *A61F 13/56* (2006.01)
  *A61F 13/53* (2006.01)
  *A61F 13/537* (2006.01)

(52) U.S. Cl.
  CPC .......... *A61F 13/5616* (2013.01); *A61F 13/53* (2013.01); *A61F 13/53747* (2013.01)

(58) Field of Classification Search
  CPC .... A61F 13/47; A61F 13/4708; A61F 13/513; A61F 13/51458; A61F 13/53; A61F 13/53747; A61F 13/5616
  See application file for complete search history.

(56) References Cited

U.S. PATENT DOCUMENTS

| | | | | | |
|---|---|---|---|---|---|
| 4,364,992 | A | * | 12/1982 | Ito .......................... | A61F 13/534 442/324 |
| 4,381,784 | A | * | 5/1983 | Aberson ................ | A61F 13/534 604/368 |
| 5,460,624 | A | * | 10/1995 | Ahr ........................ | A61F 13/474 428/198 |
| 5,763,331 | A | * | 6/1998 | Demhartner .......... | A61F 13/534 442/393 |

(Continued)

FOREIGN PATENT DOCUMENTS

CN  102961218 B  4/2014

*Primary Examiner* — Kathryn E Ditmer

(57) ABSTRACT

The invention relates to a liquid-absorbing breathable blood-resistant no-leakage sanitary pad, which consists of a skin-friendly dry layer, a breathable liquid-storage core layer, an SMS blood-resistant water-repellent non-woven fabric layer, and a bottom layer in an overlapped manner; the skin-friendly dry layer is located in the absorption surface of the breathable liquid-storage core layer, the SMS blood-resistant water-repellent non-woven fabric layer is located in the back of the breathable liquid-storage core layer, and the bottom layer is located in the breathable surface of the SMS blood-resistant water-repellent non-woven fabric layer. The SMS blood-resistant water-repellent non-woven fabric is designed in the back of the breathable liquid-storage core layer, which achieves the object of preventing water, effectively prevents the leakage of menstrual blood, so as to greatly reduce the thickness of a sanitary pad product under the premise of achieving the object of coexistence of water resistance, blood resistance, and breathability.

7 Claims, 1 Drawing Sheet

(56) References Cited

U.S. PATENT DOCUMENTS

| | | | |
|---|---|---|---|
| 2010/0152696 A1* | 6/2010 | Kudo | A61F 13/4704 604/385.14 |
| 2014/0052089 A1* | 2/2014 | Fenske | B32B 5/04 604/380 |
| 2015/0216742 A1* | 8/2015 | Johnson | A61F 13/8405 604/359 |
| 2018/0263831 A1* | 9/2018 | Manabe | A61F 13/53 |

* cited by examiner

LIQUID-ABSORBING BREATHABLE BLOOD-RESISTANT NO-LEAKAGE SANITARY PAD

TECHNICAL FIELD

The present invention relates to a liquid-absorbing breathable blood-resistant no-leakage sanitary pad which not only can quickly absorb menstrual blood, but also can effectively prevent the leakage of the menstrual blood under the premise of guaranteeing a good breathable condition, and can also greatly improve the comfort level in using of the sanitary pad, and greatly reduce the thickness of the sanitary pad. The present invention belongs to the manufacturing field of the sanitary pad.

BACKGROUND ART

The applicant possesses CN102961218B, titled "Liquid-absorbing Breathable No-leakage Sanitary Pad". The sanitary pad consists of a skin-friendly dry layer and three layers of breathable liquid-storage core layers in an overlapped manner, or consists of a skin-friendly dry layer and two layers of breathable liquid-storage core layers in an overlapped manner. Each layer of the breathable liquid-storage core layer consists of a flow-guide breathable sublayer, a liquid-storage breathable sublayer, and a water-repellent breathable sublayer in an overlapped manner; the two ends of the bottom layer of three layers of breathable liquid-storage cores are sprayed with a adhesive tape layer at intervals, and the adhesive tape layer is stuck with the release paper; the skin-friendly dry layer may be the spunlaced non-woven fabric or the perforated non-woven fabric or the perforated film, and the back of the spunlaced non-woven fabric or the perforated non-woven fabric or the perforated film is sprayed with a layer of high polymer resin.

SUMMARY OF THE INVENTION

Design object: on the basis of the background, the present invention designs a liquid-absorbing breathable blood-resistant no-leakage sanitary pad which not only can quickly absorb menstrual blood, but also can effectively prevent the leakage of the menstrual blood under the premise of guaranteeing a good breathable condition of the sanitary pad, and can greatly reduce the thickness of the sanitary pad under the premise of greatly improving the comfort level in using of the sanitary pad.

Design decision: in order to achieve the design object above, 1. the design of the SMS blood-resistant water-repellent non-woven fabric layer located in the back of the breathable liquid storage core layer 2 is a first technical feature of the present invention. The object of the design lies in that: because the total osmotic pressure of menstrual blood plasma is 313 mOsm, which is equivalent to seven atmospheric pressures (5330 millimeter of mercury, and 1 millimeter of mercury=0.133 kilopascal), and the rest is crystal osmotic pressure; while the anti-hydrostatic pressure of the SMS non-woven fabric is mmHg 20>80>110>130>150>200>220>250>280>300, which is far smaller than the total osmotic pressure of menstrual blood plasma, for an unprocessed SMS water-repellent non-woven fabric, only the water molecule can be prevented from passing through, and the menstrual blood plasma cannot be effectively prevented from passing through. However, the hydrostatic pressure mmHg 20 of the SMS non-woven fabric processed by organic fluorine is far greater than 5330 millimeter of mercury, which not only can effectively prevent the blood component of menstrual blood from passing through, but also has good breathable quality, so that the SMS non-woven fabric may not be obstructed, the weight of the SMS non-woven fabric hardly may be increased, and the SMS non-woven fabric processed by organic fluorine may not be changed into the hand feeling of the SMS non-woven fabric. Therefore, the SMS non-woven fabric processed by organic fluorine prevents the menstrual blood plasma from passing through, and ensures the water-repellent and breathable properties of the SMS non-woven fabric. The design of the SMS blood-resistant water-resistant non-woven fabric at the back of the breathable liquid storage core layer by the present application not only achieves the objects of water resistance and menstrual blood leakage prevention, but also achieves the object of coexistence of water resistance, blood resistance, and breathability. 2. The design of the SMS blood-resistant water-repellent non-woven fabric layer consisting of a layer of the SMS blood-resistant water-repellent non-woven fabric or multiple layers of SMS blood-resistant water-repellent non-woven fabrics in an overlapped manner, a second technical feature of the present invention. The object of the design lies in that: although the SMS blood-resistant water-repellent non-woven fabric can prevent the menstrual blood plasma from passing through under usual status, since the bleeding time of menstruation of a woman each month will lasts for two to seven days, and the blood loss amount each time is approximately 50 to 200 ml, only when the menstrual blood volume discharged by the woman reaches to 20 ml, there will a little menstrual blood reaching to the SMS blood-resistant water-repellent non-woven fabric, and is prevented by the SMS blood-resistant water-repellent non-woven fabric; and only when the menstrual blood volume discharged by the woman reaches to more than 20 ml, a little menstrual blood may exude from the first layer non-woven fabric in the multiple layers of the SMS blood-resistant water-repellent non-woven fabric layers under the action of mixed atmospheric pressure force at the pudendum of human body, and is prevented by the second layer. 3. The design of the polymer compound SMS non-woven fabric layer is a third technical feature of the present invention. The object of this design lies in that: because the bleeding time of menstruation of the woman each month lasts for two to seven days, and the blood loss amount is approximately 50 to 200 ml, but the blood loss amount each time cannot be determined, when using the sanitary pad, the woman sometimes is in hesitant to make a hard selection of sanitary pads with large and small absorption amount. When the sanitary pad with large absorption amount is selected, the trace of wearing the sanitary pad can be seen from the torso part of trousers after wearing the sanitary pad since the sanitary pad itself is thick, which makes woman, especially professional woman, feel embarrassment and uncomfortable, especially in spring, summer, and autumn; and when the sanitary pad with small absorption amount is selected, although the thickness is thin, and the trace of wearing the sanitary pad cannot be seen from the torso part of trousers after wearing the sanitary pad, when the uncertain menstrual blood volume reaches to more than 20 ml, a trace of exuded menstrual blood sometimes may pollute the trousers, especially the light color trousers, so as to lead to the annoyance of the woman. The present application sprays a layer of the high polymer resin between two layers of the SMS blood-resistant water-repellent compound non-woven fabrics, and because the thickness of the layer of the high polymer resin is smaller than 2 mm, the thickness of the sanitary pad is not increased greatly, so that the trace of wearing the sanitary pad can be seen from the torso part of trousers after the woman wears the sanitary pad, and the menstrual blood absorption amount of the sanitary pad is increased by about 50%, which meets the specific requirements on physiology and workplace of the woman, especially the professional woman.

Technical solutions: a liquid-absorbing breathable blood-resistant no-leakage sanitary pad consists of a skin-friendly dry layer, a breathable liquid storage core layer, an SMS blood-resistant water-repellent non-woven fabric layer, and a bottom layer in an overlapped manner; wherein the skin-friendly dry layer is located in the absorption surface of the breathable liquid storage core layer, the SMS blood-resistant water-repellent non-woven fabric layer is located in the back of the breathable liquid storage core layer, and the bottom layer is located in the breathable surface of the SMS blood-resistant water-repellent non-woven fabric layer.

Compared with the background, the present invention is different in that: on one hand, the SMS blood-resistant water-repellent non-woven fabric is designed in the back of the breathable liquid storage core layer, which achieves the object of preventing water and effectively prevents the leakage of menstrual blood, so as to greatly reduce the thickness of sanitary pad product under the premise of achieving the object of coexistence of water resistance, blood resistance, and breathability, and on the other hand, the polymer compound SMS non-woven fabric layer is designed, which reduces the thickness of the sanitary pad with large absorption amount, and ensures and increases the absorption amount of the sanitary pad with large absorption amount to the menstrual blood, so that the trace of wearing the sanitary pad cannot be seen from the torso part of trousers after a woman wears the sanitary pad during menstrual period, which meets the specific requirements on physiology and workplace of the woman, especially the professional woman.

DETAILED DESCRIPTION OF THE EMBODIMENTS

Figure 1:
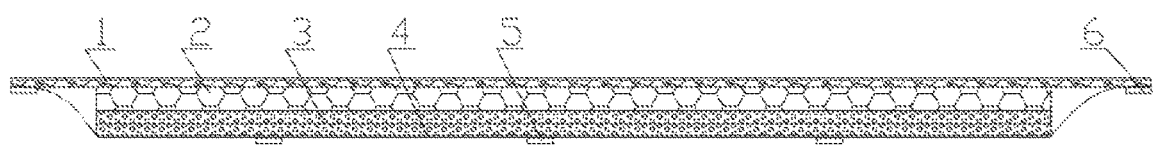
FIG. 1 is a structure diagram of a liquid-absorbing breathable blood-resistant no-leakage sanitary pad.
Figure 2:
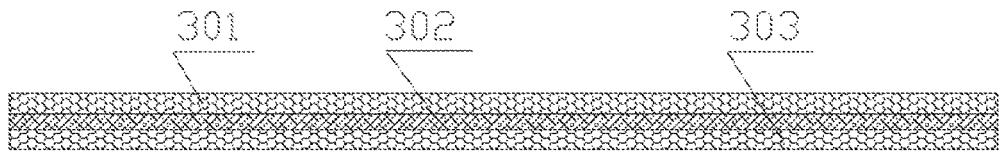
FIG. 2 is structure diagram of a compound SMS non-woven fabric layer.
Figure 3:
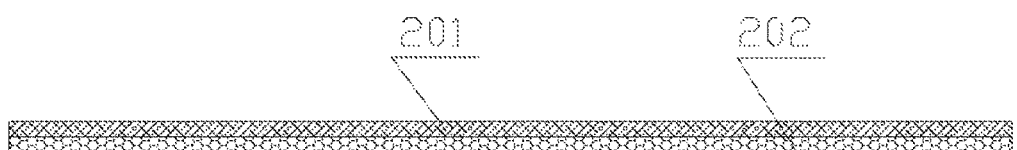
FIG. 3 is a structure diagram of a breathable liquid storage core layer.

Embodiment 1: refers to FIGS. 1-3. a liquid-absorbing breathable blood-resistant no-leakage sanitary pad consists of skin-friendly dry layer 1, breathable liquid storage core layer 2, SMS blood-resistant water-repellent non-woven fabric layer 3, and bottom layer 4 in an overlapped manner; wherein skin-friendly dry layer 1 is located in the absorption surface of breathable liquid storage core layer 2, SMS blood-resistant water-repellent non-woven fabric layer 3 is located in the back of breathable liquid storage core layer 2, and bottom layer 4 is located in the breathable surface of SMS blood-resistant water-repellent non-woven fabric layer 3. SMS blood-resistant water-repellent non-woven fabric layer 3 consists of a layer of SMS blood-resistant water-repellent non-woven fabric or multiple layers of SMS blood-resistant water-repellent non-woven fabrics in an overlapped manner. The bottom surface of bottom layer 4 is sprayed with back adhesive tapes 5 at intervals. The two sides of bottom layer 4 are sprayed with wing adhesive tapes 5 at intervals. Skin-friendly layer 1 may be a spunlaced non-woven fabric or a perforated non-woven fabric, or a perforated film. The manufacturing method of the liquid-absorbing breathable blood-resistant no-leakage sanitary pad is the prior art, and is not described in details by text herein.

Breathable liquid storage core layer 2 consists of high polymer resin layer 201 and dust-free paper 202 in an overlapped manner, and high polymer resin layer 201 is on dust-free paper 202. The top surface of breathable liquid storage core layer 2 is skin-friendly dry layer 1 and SMS blood-resistant water-repellent non-woven fabric layer 3. That is, SMS blood-resistant water-repellent non-woven fabric layer 3 is located in the back of dust-free paper 202 in breathable liquid storage core layer 2.

The gram weight of the SMS blood-resistant water-repellent non-woven fabric is 14 to 200 g/m$^2$.

Embodiment 2: on the basis of the embodiment 1, SMS blood-resistant water-repellent non-woven fabric layer 3 is the polymer compound SMS non-woven fabric layer. The polymer compound SMS non-woven fabric layer consists of the first layer of SMS blood-resistant water-repellent compound non-woven fabric 301 and high polymer resin layer 302, and the second layer of SMS blood-resistant water-repellent compound non-woven fabric 303 in an overlapped manner, wherein high polymer resin layer 302 is located between the first layer of SMS blood-resistant water-repellent compound non-woven fabric 301 and the second layer of SMS blood-resistant water-repellent compound non-woven fabric 303, and the forming manner of high polymer resin layer 302 can be shaped by laying, and can also be shaped by spraying or spraying coating.

Embodiment 3: on the basis of the embodiment 2, because the dust-free paper has high elastic force, is soft, and has excellent hand feeling and vertical sense, and has extremely high hygroscopicity and good water holding capacity, the present application can use the dust-free paper to replace high polymer resin layer 302, and the dust-free paper is located between the first layer of SMS blood-resistant water-repellent compound non-woven fabric 301 and the second layer of SMS blood-resistant water-repellent compound non-woven fabric 303, so that a trace of the menstrual blood exuded from breathable liquid storage core layer 2 is absorbed by the dust-free paper that will lock in the trace of the exuded menstrual blood to prevent further extravasation.

It should be understood that: although the embodiments above make a detailed text description to the design thought of the present invention, the text descriptions are only simple text descriptions to the design thought of the present invention instead of the limitation to the design thought of the present invention, and any combination, addition, or amendment without exceeding the design thought of the present invention shall all fall within the protection scope of the present invention.

The invention claimed is:

1. A liquid-absorbing breathable no-leakage sanitary pad, consisting of:
   a skin-friendly dry layer;
   a breathable liquid-storage core layer;
   a spunbound-meltdown-spunbound (SMS) blood-resistant water-repellent non-woven fabric layer; and
   a bottom layer,
   wherein
   the skin-friendly dry layer, the breathable liquid-storage core layer, the SMS blood-resistant water-repellent non-woven fabric layer and the bottom layer are stacked in an overlapped manner, the skin-friendly dry layer is located on an absorption surface of the breathable liquid-storage core layer, the SMS blood-resistant water-repellent non-woven fabric layer is located on a back of the breathable liquid-storage core layer, the bottom layer is located on a breathable surface of the SMS blood-resistant water-repellent non-woven fabric layer, and the SMS blood-resistant water-repellent non-woven fabric layer consists of two sheets of SMS blood-resistant water-repellent non-woven fabric sandwiching a sheet of absorbent polymer resin.

2. The liquid-absorbing breathable no-leakage sanitary pad according to claim 1, wherein the SMS blood-resistant water-repellent non-woven fabric layer is an organic fluorine processed SMS blood-resistant water-repellent non-woven fabric layer.

3. The liquid-absorbing breathable no-leakage sanitary pad according to claim 1, wherein a gram weight of the SMS blood-resistant water-repellent non-woven fabric layer ranges from 14 to 200 g/m².

4. The liquid-absorbing breathable no-leakage sanitary pad according to claim 1, wherein the bottom layer comprises adhesive stripes on a bottom surface thereof.

5. The liquid-absorbing breathable no-leakage sanitary pad according to claim 1, wherein the bottom layer comprises a wing portion extending beyond the breathable liquid-storage core layer and the SMS blood-resistant water-repellent non-woven fabric layer, and the wing portion comprises adhesive stripes on a bottom surface thereof.

6. The liquid-absorbing breathable no-leakage sanitary pad according to claim 1, wherein the skin-friendly dry layer is a spunlaced non-woven fabric or a perforated non-woven fabric, or a perforated film.

7. The liquid-absorbing breathable no-leakage sanitary pad according to claim 1, wherein the breathable liquid-storage core layer consists of an absorbent polymer resin portion and a dust-free paper portion stacked in an overlapped manner.

* * * * *